(12) United States Patent
Woo et al.

(10) Patent No.: US 6,455,067 B1
(45) Date of Patent: Sep. 24, 2002

(54) TRANSDERMAL PATCH FOR NONSTEROIDAL ANTIINFLAMMATORY DRUG(S)

(75) Inventors: Yang Pyo Woo, Choongju (KR); Sung Min Cho, Chungju (KR)

(73) Assignee: Sang-a Pharmaceutical Co., Ltd. (KR)

( * ) Notice: Subject to any disclaimer, the term of this patent is extended or adjusted under 35 U.S.C. 154(b) by 0 days.

(21) Appl. No.: 09/577,787

(22) Filed: May 24, 2000

(51) Int. Cl.[7] ............... A61F 13/00; A61K 9/70
(52) U.S. Cl. ............ 424/449; 424/484; 424/486
(58) Field of Search ............... 424/449, 484, 424/486

(56) References Cited

U.S. PATENT DOCUMENTS 5,478,568 A * 12/1995 Takayasu et al. ............ 424/449
5,976,566 A * 11/1999 Samour et al. ............ 424/449

* cited by examiner

Primary Examiner—Thurman K. Page
Assistant Examiner—Robert M. Joynes
(74) Attorney, Agent, or Firm—Seed Intellectual Property Law Group PLLC

(57) ABSTRACT

This invention relates to an external patch for an antiinflammatory drug containing nonsteroidal antiinflammatory drug which is excellent in the dermal absorption and the skin adhesion, has hardly the skin stimulus. The nonsteroidal antiinflammatory drug composition comprised of nonsteroidal antiinflammatory drug, alkylpyrrolidone, hydrophilic polyethyleneglycol and hydrophilic nonionic surfactant was diffused in the water containing base comprised of water soluble polymer material, water soluble vinyl polymer and water insoluble multivalent metallic salt to provide the external patch containing nonsteroidal drug dissolved and diffused in the water containing base in the microemulsion state, which is excellent in the dermal absorption and also good in the skin adhesion, has hardly the skin irritations.

18 Claims, 1 Drawing Sheet

TRANSDERMAL PATCH FOR NONSTEROIDAL ANTIINFLAMMATORY DRUG(S)

BACKGROUND OF THE INVENTION

1. Field of the Invention

This invention relates to transdermal patch for delivery of a nonsteroidal antiinflammatory drug, which is used in inflammatory diseases such as deformative arthritis, articulatio humeri periphery inflammation, myalgia, contusion, sprain, backache, and so on.

2. Description of the Prior Art

Nonsteroidal antiinflammatory drugs have powerful antiinflammatory action and alleviat pain. Lately, in the orthopaedic surgery field, they are representative drugs for treating deformative arthritis, articulatio humeri periphery inflammation, tendinitis, tendosynovitis, peritendinitis, myalgia and the like. However, when they are taken orally as a tablet or capsule, or injected into the muscles, they can cause digestive trouble, liver trouble or systemic adverse effects because they are absorbed through the gastrointestinal tract. Therefore, to mitigate these adverse effects, in the case where they do not need to be administered to the whole body because the inflamed part is local and occurs relatively near to the body the surface, local agents, for example, the external patches such as a poultice or plaster, or the dermal absorption agents such as ointment, cream or gel have been developed and are used, of which most drug components act only in a limited way on the affected part and its surroundings to give a local effect.

Among these dermal absorption agents, ointments are applied easily even in active parts such as arthritis but the administration amount is not exact, the drug effect is not continued, and the drug effect may be reduced by the loss of drug due to contact with the patient's clothes or the other irritation during the administration. The patches have a problem in maintaining their adhesion to the skin but, compared to the ointment, the administration amount is exact, the drug effect lasts and the control of the drug administration is easy. For the reason of the pharmaceutical preparation's property, patches, relative to ointments, are used more in shoulder pain, neuralgia, arthralgia, backache and the like. As representative examples, there are the patches of nonsteroidal antiinflammatory drugs such as ketoprofen, indomethacin, flurbirprofen, piroxicam, ferbinac and the like.

A basic consideration points in developing these antiinflammatory drugs, first of all, the drug should be released continuously, and then the released drug should rapidly penetrate the corneum to be absorbed into the affected tissue, the corneum being a powerful obstacle for skin permeation, and the patch components should not adversely effect the skin as to skin irritation, and the like, in adbering the patches to the skin. Various methods of making these patches for antiinflammatory drug have been developed, for example, the drug solubility in a base was increased to accelerate the drug movement as described in Japanese Patent Laid-Open No. sho 63-88125 or sho 57-140711; the drug release in the base was increased as described in Japanese Patent Laid-Open No. Pyong 6-247856 or pyong 4-173731; a drug in the base was made nearly in the state of saturated solubility in order to accelerate the drug release into the corneum from the base as shown in Japanese Patent Laid-Open No. sho 60-185713; an absorption agent befacient was used to promote the dermal absorption of the drug component as described in Japanese Patent Laid-Open No. sho 57-75918 or 56-169623; and others such as the water retention of the base was increased to hydrate or soften the stratum corneum or the adhesion to the skin is raised to accelerate the dermal absorption.

However, in the case where the patch including a nonsteroidal antiinflammatory drug is manufactured according to the proposed methods as above, for instance, that it is mixed in a base including a large quantity of moisture like a poultice, since most of drugs are insoluble in water to be deposited in the base, the drugs' movements are restrained and the delay of the drug release hinders the rapid effect of the drug. Also, in attaching it to the skin, the pharmaceutical preparation is not completely in contact with the skin, whereby a sufficient quantity of drug is not transported to the skin, as a result, the drug action may be lowered. In addition, they are troublesome to use and not economical such that the separate patch supplementary member like an adherent cloth should be used to fix the pharmaceutical preparation to the skin. Besides, when it is mixed in an oil-soluble adherent base such as a plaster, it can raise the drug solubility in the base but gradually the drug is precipitated, and because of the strong skin-adhesion, the adverse effect such as itching or erythema can easyly appear. Also, when the pharmaceutical preparation is removed from the skin, the pain due to the physical irritation or the damage to the corneum may be occur. In the summer season or when sweating, due to the skin secretion, the patch is easily falls off the skin. Thus, a new pharmaceutical preparation is to solve the above problems is needed.

SUMMARY OF THE INVENTION

This invention is designed to solve the problems as above, the object of the invention is to provide a dermal absorption type patch with the drug component being a nonsteroidal antiinflammatory drug which is excellent in being released from the base and absorbed through the skin and which provides good skin adhesion, without skin irritation and is pharmaceutically stable.

BRIEF DESCRIPTIONS OF THE DRAWINGS

DESCRIPTION OF THE PREFERRED EMBODIMENT

Figure 1:
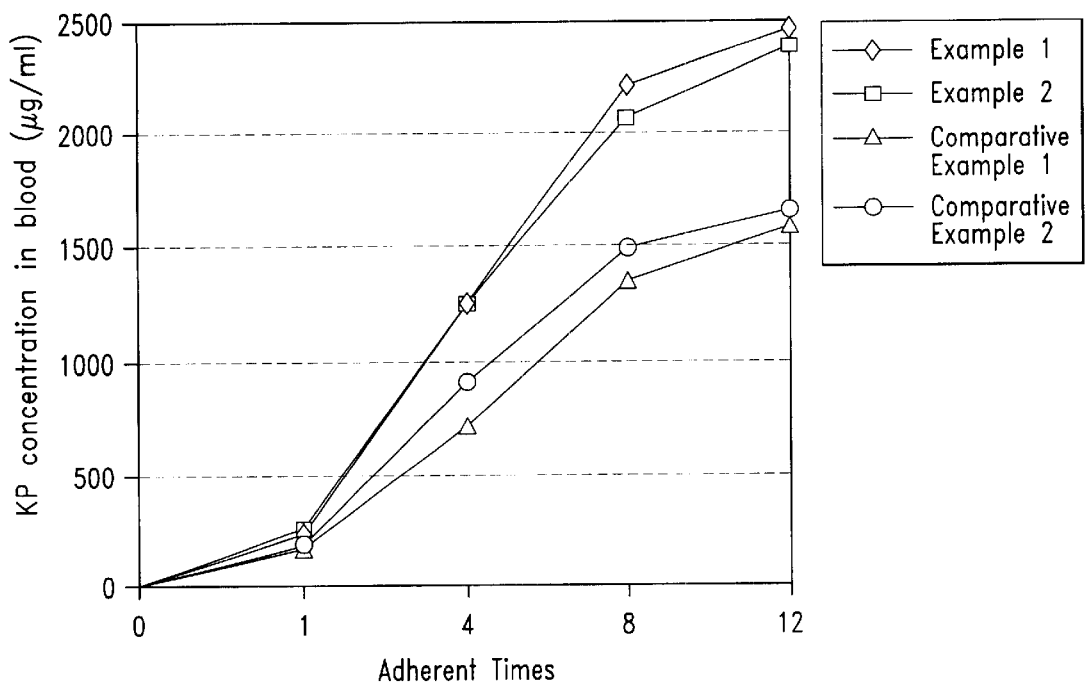
FIG. 1 is a graph showing the test results of the dermal absorption in vivo.

The present inventor has investigated this area for a long time to achieve the above objects, and, as a result, found that when a nonsteroidal antiinflammatory drug is dissolved in the composition comprising alkyl-pyrrolidone, hydrophilic polyethylene glycol, hydrophilic nonionic surfactant, and the like, to be diffused in a specific mixed water containing base, the nonsteroidal antiinflammatory drug is stably dissolved and diffused in the water containing base in almost a microemulsion state, whereby the invention provides a transdermal patch including a NSID, such as ketoprofen, which is excellent in the release of drug and dermal absorption, has no physical irritation due to skin adhesion and is pharmaceutically stable.

The transdermal patch of the nonsteroidal antiinflammatory drug according to the invention comprises a nonsteroidal antiinflammatory drug active component 0.1~1.0 weight %, alkyl-pyrrolidone 0.5~10 weight %, hydrophilic polyethylene glycol 1~15 weight %, hydrophilic nonionic surfactant 0.01~3 weight %, water soluble polymer having carboxyl group 2~15 weight %, water soluble vinyl polymer 0.1~10 weight %, water insoluble multivalent metallic salt 0.01~10 weight %, multivalent alcohol 4~40 weight % and organic hydroxy acid and water.

More particularly, the nonsteroidal antiinflammatory drug containing solution comprising of a nonsteroidal antiinflammatory drug, a alkyl-pyrrolidone, a hydrophilic polyethylene glycol and a hydrophilic nonionic surfactant is diffused in a series of water containing base consisting of the specific components, i.e., water soluble high polymer having carboxyl group, water soluble vinyl polymer, water insoluble multivalent metallic salt, humectant such as multivalent alcohol, organic hydroxy acid and water is disclosed. After the nonsteroidal antiinflammatory drug is stably diffused in the water containing base in the macroemulsion state, it is solidified to be coated on a nonwoven fabric to provide the patch. The patch according to the invention maintains its form even without inorganic packing material, such as kaolin, titan white or zinc white, or thermoplastic polymer such as gelatin, which are generally used in the traditional patches. Also, the patch of the invention is excellent in releasing the drug for dermal absorption; adheres well to the skin; and does not irritate the skin. In addition, it has almost a transparent appearance; is pharmaceutically stable; has a physical compression effect so as to press the affected part continuously; and a rapidly adsorbs waste products like sweat secreted from a skin surface.

The active component included as the nonsteroidal antiinflammatory drug (hereinafter, it is "NSAID") of this invention is selected from ketoprofen, flurbirprofen, piroxicam, tenoxicam, diclophenac, and ferbinac. Since most of them are water insoluble, the powder itself can not be applied to the water containing base. If the powder itself is applied, homogeneous diffusion is difficult and also the drug movability in the base is lowered, whereby it is difficult to obtain a sufficient drug effect. To stably maintain the active component and promote the drug release and dermal absorption, the active component should be homogeneously dissolved or diffused in the base. For that, a separate solubilizer or stabilizer should be added. As a solvent, there are hydrophilic glycols such as polyethylene glycol, polypropylene glycol, polybutylene glycol and like, and alkyl-pyrrolidones, such as methyl-pyrrolidone, ethyl-pyrrolidone, 2-hydroxyethyl-pyrrolidone and the like. As a stabilizer, a hydrophilic surfactant is used. These solubilizers or stabilizers are preferably used in combination. When they are used separately, there are problems in that the active components are recrystallized in the water containing base or dermal absorption is lowered. A hydrophilic nonionic surfactant is the most preferable solubilizer.

The blending amount of the active component of this invention is 0.01~2.0 weight % to the whole solid, preferably 0.1~1.0 weight %. If the blending amount is below 0.01 weight %, it is difficult to show the drug effect. On the contrary, if it is above 2.0 weight %, the active component is easyly deposited in the water containing the adhesive base which does not promote the drug effect.

As for the alkyl-pyrrolidone used in this invention, there are methyl-pyrrolidone, ethyl-pyrrolidone, 2-hydroxyethyl-pyrrolidone and the like. These alkylpyrrolidones are ambipolar material which is compatible in water or oil to dissolve the NSAID very well but, in the case of being a contact with water, it causes the NSAID to crystallize. Therefore, since it is difficult to stably maintain the NSAID in a water containing base by mixing only alkyl-pyrrolidone, other separate additives should be used in combination, at this time, as the additives, a hydrophilic polyethylene glycol or a hydrophylic nonionic surfactant is preferable. The alkylpyrrolidone acts not only as a solubilizer but also as an absorption agent an absorbefacient. One or two more among methyl-pyrrolidone, ethyl-pyrrolidone and 2-hydroxyethyl-pyrrolidone are mixed, with the mixing amount being 0.5~10 weight % to the whole solid. If the amount of the alkylpyrrolidone is too much, the use feeling deteriorates.

As the hydrophilic polyethylene glycol used in this invention, there are various types according to the molecular weight but among them the polyethylene glycol 400 which is in a liquid state at the room temperature is the most preferable. The hydrophilic polyethylene glycol goes well with the water containing base. It is the solution supplement agent and the solvent of the NSAID, and prevents the NSAID from precipitating in the water containing base into a crytal and promotes the dermal absorption. It does not matter that the mixing amount of polyethylene glycol is above that of the active component, however, it is preferably 1~15 weight % to the whole solid. If the mixing amount of polyethylene glycol is below 1%, the NSAID is precipitated in the water containing base, if it is too much, the use feeling of the pharmaceutical preparation deteriorates. Another dihydric alcohol, such as polypropylene glycol or polybutylene glycol can be used in place of the polyethylene glycol types.

The hydrophilic nonionic surfactant used in this invention is preferably above a hydrophilic-lipophilic balance of 10 (HLB 10). The hydrophilic nonionic surfactants for use in the present invention include polyoxyethylene glycerin fatty acid ester, polyoxyethylenesorbitol fatty acid ester, polyoxyethylenesorbitol fatty acid ester, polyoxyethylene glycol fatty acid ester, polyoxyethylene castor oil/or curing castor oil, polyoxyethylenealkyl ester, polyoxyethylenealkylphenyl ether, polyoxyethylene polyoxypropylenealkyl ether and the like. Such hydrophilic nonionic surfactants reduce the surface tension of water to diffuse the NSAID into the water containing base, with alkyl-pyrrolidone and polyethylene glycol, to prevent it from crystallizing out in the water containing base. The mixing amount of the hydrophilic nonionic surfactant to the whole solid is generally 0.01~5 weight %, preferably 0.01~3 weight %. If the amount of the hydrophilic nonionic surfactant is much less than 0.01 weight %, the active component is not stably maintained in the water containing base, drug diffusion may be lowered, on the contrary, if it is more than 5 weight %, the use feeling deteriorates such that the pharmaceutical preparation is sticky.

The water soluble polymer material having a carboxyl group and/or its salt used in this invention includes natural, synthetic or semisynthetic polymers provided that the water soluble polymer and/or its salt should have carboxyl group on its molecular chain. However, among them, sodium polyacrylate or partial neutralization of the sodium polyacrylate, carboxyethyl cellulose are suitable but as the water soluble polymer having a carboxyl group in the molecule, polyacrylic acid, polymetacrylic acid, carboxyvinyl polymer, sodium carboxymethyl cellulose, sodium polyacrylate, partial neutralization of sodium polyacrylate, methoxyethylene which hydrolyzes in water to provide a carboxyl group or anhydrous maleic acid copolymer can be used. They are used alone or in combination, the mixing amount to the whole solid is 2~15 weight %, preferably 3~13 weight %. If it is less than 2 weight %, the maintainability of the solid form decreases, also if it is more than 15 weight %, the viscosity during the patch manufacturing process is too high, whereby the combination becomes difficult to process.

The water soluble vinyl polymer used in this invention includes polyvinyl alcohol, polyvinyl-pyrrolidone, vinyl-pyrrolidone/vinyl acetate copolymer. They are used either alone or in combination of two or more. The mixing amount to the whole solid is 0.1~10 weight %, preferably 1~7 weight %. If the mixing amount is below 0.1 weight %, the promotion effect of the skin adhesion and the maintainability of the form of the base itself does not occur, also if it is above 10 weight %, the combination is difficult to process, and the cohesion of the water containing base itself is too strong, whereby it weakens the adhesion property to the skin.

The water insoluble multivalent metallic salt used in this invention is a crosslink agent, for example, trivalent aluminum compounds such as aluminum hydroxide, aluminum sulfide, aluminum nitrate, aluminum acetate, sodium aluminate and aluminum glycinate; divalent magnesium compound such as magnesium hydroxide, magnesium sulfide, magnesium carbonate and magnesium nitrate; and divalent calcium compounds such as calcium hydroxide, calcium carbonate, calcium nitrate, calcium citrate, calcium panthothenate. If these multivalent metallic salts are contacted with an acid, metallic ions are slowly dissolved. The dissolved metallic ions react with the water soluble polymer having a carboxyl group(s) on its molecular chain to form a homogeneous water containing gel. One or two or more selected from them may be mixed together. The mixing amount to the whole solid is 0.01~10 weight % for supporting and maintaining the gel form. If the mixing amount is below 0.01 weight %, the crosslink is not sufficiently formed, whereby the strength of the gel is lowered and the maintenance of the obtained gel form itself is remarkably lowered, if it is more than 10 weight %, the water containing base is hardly cured resulting poor flexibility, adhesion, drug release and molding processing. Other than the above multivalent metallic salt compound, alum types such as aluminum alum, iron alum and the like, or the multivalent metallic salt of the antacid types, including aluminum and magnesium, can be also used.

As an organic hydroxy acid used in this invention, tartaric acid, citric acid, lactic acid, malic acid and gluconic acid together with multivalent metallic salt maintain and strengthen the form of the water containing base, have an effect on the pH of the water containing base, the multivalent metallic salt, the chelate forming, the stability of the NSAID including a ketoprofen. The mixing amount is suitable in the degree that the pH of the solid can be maintained at 4.5~7.0.

The multivalent alcohol used in this invention influences the flexibility, the humidity of the water containing base, the adhesion after a damp proofing, and the aging stability. Said multivalent alcohol also serves as a good dispersion agent of a water-soluble polymer during the patch manufacturing process. Exemplary multivalent alcohols include divalent alcohols such as ethylene glycol, propylene glycol, 1,3-butanediol, triethylene glycol and the like; trivalent alcohols such as glycerin, trihydroxyisobutane and the like; quadrivalent alcohols such as erythritol, pentaerythritol and the like; pentavalent alcohols such as xylitol, adonitol and the like; and hexavalent alcohols such as sorbitol, mannitol and the like. The mixing amount to the whole solid amount is 5–50 weight %, preferably 10–40 weight %.

The water used in this invention hydrates and softens the corneum to promote the dermal absorption of the NSAID and cools the affected part enhance the drug effect. The mixing amount to the whole base is generally 15~80 weight %, preferably 30~70 weight %. If the water amount is 15 weight % or less, the skin hydration effect is lowered, if it is too high, the maintenance form of the water containing gel base remarkably deteriorates.

In this invention, for strengthening the water retention, the processing and the plasticity, without influencing the effect of the invention, a nonorganic packing material such as kaolin, talc, bentonite, titanium oxide, potassium bicarbonate, anhydrous silicic acid, zinc oxide, silica or alumina; a natural polymer such as gelatin, casein, sodium alginate, locustbin gum, jantan gum, agar, pectin, arabia gum, carageennan, tragacantha, dextrin and chitin; a semi-synthetic polymer such as methyl cellulose, ethyl cellulose, hydroxypropyl cellulose, hydroxypropylmethyl cellulose, acrylic acid-starch graft copolymer and crosslink gelatin; or a synthetic polymer such as polyvinyl acetate-acrylic acid copolymer, pyrrolidone-ethyl acrylic acid copolymer and butylmetacrylic acid copolymer can be used. If necessary, various components which are used in cosmetics or pharmaceutics, i.e., an antiseptic, an antioxidant, a pH controlling agent, chelating agent, aromatic oil componet, aromatics, colorant and like conditioner adjuster also can be added.

The patch according to this invention is provided by the following methods: the solid including the NSAID is delivered directly onto a supporter or it is first coated on a film for peeling and then is transcribed to a supporter to make the solid on the supporter; and then, a peeling film which can be peeled in using is attached thereon. In this case, which of a fabric cloth such as a lint, a nonwoven fabric or a knitted fabric as the supporter can be used, particularly it is preferred that it has expansion and contraction in two directions. It does not matter that the fiber constituting a fabric cloth, a nonwoven fabric and a knitted fabric is a natural fiber such as a cotton, or a synthetic fiber such as a polyolefin, polyester or nylon.

The present invention, especially the patch containing a ketoprofen among the NSAID, is described in more detail by the following examples, but this invention is not limited to the patch containing ketoprofen(hereinafter, "KP"). In the below examples, % is weight % if it is not mentioned.

The patch formulations according to each example and comparative example are written in the below table 1.

TABLE 1

| Component | (weight %) | | | | | | |
|---|---|---|---|---|---|---|---|
|  | Ex. 1 | Ex. 2 | Ex. 3 | Ex. 4 | C. Ex. 1 | C. Ex. 2 | C. Ex. 3 |
| Ketoprofen | 0.3 | 0.3 | 0.3 | 0.3 | 0.3 | 0.3 | 0.3 |
| Polysorbate #80 | 0.5 | 0.5 | — | — | 0.5 | — | — |
| POE (4) Lauryl ether | — | — | 0.5 | 0.5 | — | 0.5 | — |
| Methyl Pyrrolidone | 3.0 | 1.0 | — | 2.0 | 3.0 | 3.0 | — |
| Ethyl Pyrrolidone | — | 2.0 | 3.0 | 1.0 | — | — | 3.0 |
| PEG #400 | 10.0 | 10.0 | 10.0 | 10.0 | — | — | 10.0 |
| CMC-Na | 4.0 | 4.0 | 4.0 | 4.0 | 4.0 | 4.0 | 4.0 |
| Na - Polyacrylate | 6.0 | 5.5 | 5.5 | 6.0 | 6.0 | 5.5 | 6.0 |
| Sanwet 1M-1000PS | — | 0.5 | 0.5 | — | — | 0.5 | — |
| Polyvinyl Alcohol | — | 1.0 | 1.0 | — | 1.0 | — | — |
| PVP/VA Copolymer | 4.0 | 3.0 | 3.0 | 4.0 | 3.0 | — | — |

TABLE 1-continued (weight %)

| Component | Ex. 1 | Ex. 2 | Ex. 3 | Ex. 4 | C. Ex. 1 | C. Ex. 2 | C. Ex. 3 |
|---|---|---|---|---|---|---|---|
| Al (OH)$_3$ Gel Dried | 0.2 | 0.2 | 0.2 | 0.2 | 0.2 | 0.2 | 0.2 |
| Methyl paraben | 0.1 | 0.1 | 0.1 | 0.1 | 0.1 | 0.1 | 0.1 |
| Kaolin | — | — | — | — | — | — | 4.0 |
| EDTA-2Na | 0.5 | 0.5 | 0.5 | 0.5 | 0.5 | 0.5 | 0.5 |
| Tartaric Acid | 2.2 | 2.2 | 2.2 | 2.2 | 2.2 | 2.2 | 2.2 |
| Gelatin | — | — | — | — | — | 4.0 | — |
| Glycerin Conc | 28.0 | 28.0 | 28.0 | 28.0 | 28.0 | 28.0 | 28.0 |
| H$_2$O | qs | qs | qs | qs | qs | qs | qs |

EXAMPLE 1

According to the mixing amount shown in the table 1, the PVP/VA(Poly Vinyl Pyrrolidone/Vinyl Acetate) Copolymer was stirred and dissolved in a proper purified water. EDTA-2Na, tartaric acid, dried Al(OH)$_3$Gel were added thereto and stirred sufficiently. The glycerin-paste comprised of Na-polyacrylate, CMC-Na and methyl-paraben diffused in glycerin Conc. and the KP mixed solution in which KP, polysorbate #80, methyl-pyrrolidone and PEG #40 were homogeneously mixed were added thereto. Until the mixed solution was homogeneous, it was obtained as a solid.

The solid was coated on the nonwoven fabric to 715 g/m$^2$, the plastic film was coated on the surface thereof. It was cut to 10.14 cm$^2$ to give the ketoprofen patch of the present invention.

EXAMPLE 2

According to the mixing amount shown in the table 1, PVP/VA Copolymer and polyvinyl alcohol were stirred and dissolved in a proper purified water. EDTA-2Na, tartaric acid and dried Al(OH)$_3$Gel were added thereto and stirred sufficiently. The glycerin-paste comprised of Na-polyacrylate, CMC-Na Sanwet 1M-1000mps and methyl-paraben diffused in glycerin Conc. and the KP mixed solution in which KP, polysorbate #80, methyl-pyrrolidone, ethyl-pyrrolidone and PEG #400 have been homogeneously mixed were added thereto. Until it was homogeneous, the mixed solution was unified to give a solid. Hereafter, the ketoprofen of the present invention was obtained by the same method with the example 1.

EXAMPLE 3

According to the mixing amount shown in the table 1, PVP/VA Copolymer and polyvinyl alcohol were stirred and dissolved in a proper amount of purified water. EDTA-2Na, dried Al(OH)$_3$Gel and tartaric acid were added thereto and stirred sufficiently. The glycerin-paste comprised of Na-polyacrylate, CMC-Na, Sanwet 1M-1000mps and methyl-paraben diffused in glycerin Conc and a KP mixed solution in which KP, POE(4) lauryl ether, ethyl-pyrrolidone and PEG #400 have been homogeneously mixed were added thereto. Until it was homogeneous, the mixed solution was obtained as a solid. Hereafter, the ketoprofen of the present invention was obtained by the same method with the example 1.

EXAMPLE 4

According to the mixing amount shown in the table 1, PVP/VA Copolymer was stirred and dissolved in a proper amount of purified water. EDTA-2Na, dried Al(OH)$_3$Gel and tartaric acid were added thereto and stirred sufficiently. Glycerin-paste comprised of Na-polyacrylate, CMC-Na and methyl-paraben diffused in glycerin Conc and the KP mixed solution in which KP, POE(4) lauryl ether, methyl-pyrrolidone, ethyl-pyrrolidone and PEG #400 have been homogeneously mixed were added thereto. Until it was homogeneous, the mixed solution was obtained as a solid. Hereafter, the ketoprofen containing patch of the present invention was obtained by the same method with the example 1.

EXAMPLE 5

The flurbirprofen containing patch of the present invention was obtained according to the same method with the example 1 except that a flurbirprofen instead of a ketoprofen was used as an active component.

EXAMPLE 6

The pyroxicam containing patch of the present invention was obtained according to the same method with the example 1 except that a pyroxicam instead of a ketoprofen was used as an active component.

EXAMPLE 7

The tahenoxicm containing patch of the present invention was obtained according to the same method with the example 1 except that a thenoxicam instead of a ketoprofen was used as an active component.

EXAMPLE 8

The diclophenac containing patch of the present invention was obtained according to the same method with the example 1 except that a diclophenac instead of a ketoprofen (KP) was used as an active component.

EXAMPLE 9

The ferbinac containing patch of the present invention was obtained according to the same method with the example 1 except that a ferbinac instead of a ketoprofen(KP) was used as an active component.

COMPARATIVE EXAMPLE 1

According to the mixing amount shown in the table 1, PVP/VA Copolymer and polyvinyl alcohol were stirred and dissolved in a proper purified water. EDTA-2Na, dried Al(OH)$_3$Gel and tartaric acid were added thereto and stirred sufficiently. The glycerin-paste comprised of Na-polyacrylate, CMC-Na anc methyl-paraben diffused in glycerin Conc and the KP mixed solution in which KP, polysorbate #80 and methyl-pyrrolidone have been homogeneously mixed were added thereto. Until the mixed solution was homogeneous, it was obtained as a solid.

Hereafter, the ketoprofen patch of the present invention was obtained by the same method with the example 1.

COMPARATIVE EXAMPLE 2

According to the mixing amount shown in the table 1, gelatin was stirred and dissolved in a proper amount of a purified water heated to 40° C. EDTA-2Na, dried Al(OH)$_3$ Gel and tartaric acid were added thereto and stirred sufficiently. The glycerin-paste comprised of Na-polyacrylate, Sanwet 1M-1000mps, CMC-Na and methyl-paraben diffused in glycerin Conc and the KP mixed solution in which KP, POE(4) lauryl ether and methyl-pyrrolidone have been homogeneously mixed were added thereto. Until the mixed solution was homogeneous, it was unified to give a solid.

Hereafter, the ketoprofen patch of the present invention was obtained by the same method with the example 1.

COMPARATIVE EXAMPLE 3

According to the mixing amount shown in the table 1, CMC-Na was stirred and dissolved in a proper amount of purified water. EDTA-2Na, dried Al(OH)$_3$Gel and tartaric acid were added thereto and stirred sufficiently. The glycerin-paste comprised of Na-polyacrylate, CMC-Na, kaolin and methyl-paraben diffused in glycerin Conc. and the KP mixed solution in which KP, ethyl-pyrrolidone and PEG #400 have been homogeneously mixed were added thereto. Until the mixed solution was homogeneous, it was obtained as a solid.

Hereafter, the ketoprofen patch of the present invention was obtained by the same method with the example 1.

Hereafter, the drug release and the dermal absorption, the skin irritation, the skin adherent state and the stability of the pharmaceutical preparation stability were estimated with the patches of the above examples and comparative examples.

Test 1

Dermal Absorption Experiment

To confirm the drug release and the dermal absorption, the dermal absorption experiment in vivo was carried by using a rat. Sprague Dowly Family Rat(weight 180~220 g) as an experimental animal constituted a group of five rats. In the day before coating the specimen, the rat was anesthetized with ether. The back fur of each animal was removed with an electrical razor or an electrical cutter. The patches of examples 1, 2 and comparative examples 1,2 were ripened for one month and more and cut to 7 cm×5 cm respectively. The specimen was fixed on the back of a rat by a medical band. After one hour, four hours, eight hours and twelve hours from attaching the patch, the blood of the rat was taken and the drug concentration in plasma was assayed by the high speed liquid chromatography method. The experimental result is shown in table 2 and in FIG. 1, provided that the numbers represent the average and the standard error of every samples 5. As known from this result, the KP concentration of the patch according to the present invention is higher than that of comparative examples. These results prove that the patch according to the present invention was excellent in the drug release and the dermal absorption.

Test 2

Drug Action Pharmacological Experiment (Antiinflammatory Experiment)

Figure 2:
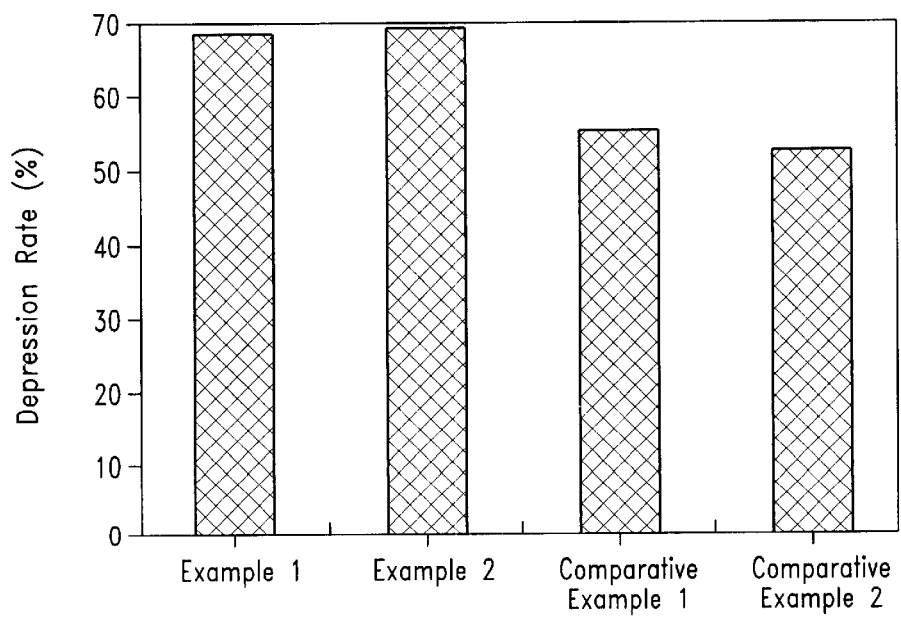
FIG. 2 is a graph showing the results of the blood vessel permeability inhibition test of F-BSA by ketoprofen in Carragennin Induced Air-Pouch Inflammation Model.

The antiinflammatory effect was confirmed with a rat through the blood vessel permeability restraint experiment by the Carragennin induced Air-Pouch Inflammation Model. Sprague Dowly family Rat(weight 180~220 g) as an experimental animal constituted one group of seven rats. In the day before coating the specimen, the rat was anesthetized with ether. The back fur of each animal was removed with an electrical razor or an electrical cutter. 8 ml of air was hypodermically injected at the center of the back. In the next day, 4 ml of 2% carragennin saline water(37° C.) was injected in the Air-Pouch, immediately after that, the specimen was coated and then fixed by a medical band. The patches of the examples 1,2 and the comparative examples 1,2 were cut to the 7 cm×5 cm size respectively and then used as a specimen. Separately, a group of specimens which were not coated was also examined as a control. In six hour after coating the specimen, 0.3 ml of 1% F-BSA (Fluorosceinisthiocyanate Bovine Serum Albumin) solution dissolved in Tyrode's solution was injected to the veins of the femoral region. After 30 minutes, the rats were killed by removing blood and the amount of the fluorescent material in the pouch effusion and the amount of the ketoprofen were measured. The result was shown in tables 3a, 3b and in FIG. 2. Provided that the numbers showed the average and the standard error of the whole samples 7, these results prove that the KP amount of the patch of the present invention was more than that of the comparative examples, and the present invention was excellent in the antiinflammatory effect because it prevented the blood vessel permeation of the F-BSA.

TABLE 3a

The F-BSA amount in the pouch effusion by the Carragennin induced Air-Pouch inflammation Model

| Specimen | F-BSA injection amount | F-BSA amount (μg) | Depression rate (%) |
| --- | --- | --- | --- |
| No treatment | 3 mg | 18.6 ± 4.5 | 0 |
| Example 1 | 3 mg | 5.9 ± 0.5 | 68.3 |
| Example 2 | 3 mg | 5.7 ± 0.4 | 69.3 |
| Comp. Example 1 | 3 mg | 8.4 ± 1.1 | 54.8 |
| Comp. Example 2 | 3 mg | 8.9 ± 1.3 | 52.2 |

TABLE 2

Ketoprofen concentration in blood by a dermal absorption in vivo

| | Adherent time | | | | |
| --- | --- | --- | --- | --- | --- |
| Specimen | 1 hour (ng/ml) | 4 hours (ng/ml) | 8 hours (ng/ml) | 12 hours (ng/ml) | AUC Relative ratio |
| Example 1 | 257 ± 19 | 1,226 ± 38 | 2,185 ± 56 | 2,424 ± 45 | 162.2 |
| Example 2 | 225 ± 21 | 1,250 ± 45 | 2,054 ± 47 | 2,357 ± 57 | 156.7 |
| Comparative Example 1 | 154 ± 12 | 694 ± 32 | 1,330 ± 41 | 1,578 ± 81 | 100.0 |
| Comparative Example 2 | 173 ± 14 | 894 ± 48 | 1,459 ± 50 | 1,626 ± 76 | 110.5 |

TABLE 3b

The KP amount in the pouch effusion by the Carragennin induced Air-Pouch inflammation Model

| Specimen | KP administration amount | KP amount ($\mu$g) | Relative comparison |
|---|---|---|---|
| No treatment | 0 | 0 | 0 |
| Example 1 | 7.5 mg/5 × 7 cm$^2$ | 7.0 ± 0.2 | 118.6 |
| Example 2 | 7.5 mg/5 × 7 cm$^2$ | 6.9 ± 0.2 | 116.9 |
| Comp. Example 1 | 7.5 mg/5 × 7 cm$^2$ | 5.7 ± 0.4 | 96.6 |
| Comp. Example 2 | 7.5 mg/5 × 7 cm$^2$ | 5.9 ± 0.3 | 100.0 |

Test 3

Skin Irritation Test

The skin stability was confirmed by the skin first irritation test. The 20 persons adult men and women(12 men and 8 women) of good health were selected and divided into two groups of 10 persons each having the same numbers of men and women, the patches of the example 1 and the comparative example 1 were attached and fixed with an adherent fabric to the left and right back of the first group respectively. And the patches of the example 3 and comparative example 3 were attached and fixed with an adherent fabric to the left and right back of the second group, respectively. After 24 hours from the time of attachment of the patch, the specimens were removed, and the skin where the patch was attached after one and 24 hours was observed with the eye and decided according the criterion of the table 4. The skin irritation index was produced with taking marks from the strong reaction. These values were estimated according to the stimulation index criterion of the table 5. As shown in the table 6, it was confirmed that all the patches of the examples and the comparative examples had low PII, very little irritation and was safe.

Skin irritation index(PII)=(Average total of strong reaction in 1 hour, 24 hours after removing/test total)×100

TABLE 4

| Skin state | Criterion Evaluation mark |
|---|---|
| No reaction | 0 |
| Weak erythema (hardly judgement) | 1 |
| Sure erythema | 2 |
| Erythema + edema, papule + vesication | 4 |
| Bulla | 5 |

TABLE 5

First skin irritation index

| Stability section | PII |
|---|---|
| Weak Stimulus | 0 ~ 2 |
| Middle stimulus | 3 ~ 5 |
| Strong stimulus | 6 ~ 8 |

TABLE 6

Skin stimulation test

| Testee Number | Exam. 1 30 min. | Exam. 1 24 hr. | Comp. Exam. 1 30 min. | Comp. Exam. 1 24 hr. | Exam. 3 30 min. | Exam. 3 24 hr. | Comp. Exam. 3 30 min. | Comp. Exam. 3 24 hr. |
|---|---|---|---|---|---|---|---|---|
| 1 | 0 | 0 | 0 | 0 | 0 | 0 | 0 | 0 |
| 2 | 0 | 0 | 0 | 0 | 0 | 0 | 0 | 0 |
| 3 | 0 | 0 | 0 | 1 | 0 | 0 | 0 | 0 |
| 4 | 0 | 0 | 0 | 0 | 0 | 1 | 0 | 0 |
| 5 | 0 | 0 | 0 | 0 | 0 | 0 | 1 | 0 |
| 6 | 0 | 0 | 0 | 0 | 0 | 0 | 0 | 0 |
| 7 | 0 | 0 | 1 | 0 | 0 | 0 | 0 | 0 |
| 8 | 0 | 0 | 0 | 0 | 0 | 0 | 0 | 0 |
| 9 | 0 | 0 | 0 | 0 | 0 | 0 | 0 | 0 |
| 10 | 0 | 0 | 0 | 0 | 0 | 0 | 0 | 0 |
| Total | 0 | | 2 | | 1 | | 1 | |
| Incidence (%) | 0/10 (0%) | | 2/10 (%) | | 1/10 (10%) | | 1/10 (10%) | |
| PII | 0 | | 0.2 | | 0.1 | | 0.1 | |

Test 4

Skin Adherent Test

The skin adhesion was estimated with the skin adherent state after attaching it directly to people. 40 Persons consisting of adult men and women of good health were selected and divided into two groups of 20 Persons, each group comprising the same number of men and women. The patches of the example 1 and the comparative example 1 were attached to the left and the right shoulder of the first group respectively. And the patches of the example 3 and comparative example 3 were attached to the left and the right knee of the second group respectively. While avoiding violent exercise, they lived the usual everyday life. After 8 hours, the skin adherent state was estimated by viewing the patchs. The result are shown in table 7. As shown in the table 7, the patch according to the present invention was better in the skin adherent state and was excellent in the skin adhesion, than that of the comparative example.

TABLE 7

Skin adherent test

| Adherent state/ Adherent part and specimen | Shoulder Ex. 1 | Shoulder C. Ex. 1 | Knee Ex. 3 | Knee C. Ex. 3 |
|---|---|---|---|---|
| Almost whole faces was adherent closely to skin (good) | 10 | 2 | 8 | 1 |
| 3/4 of applied area was adherent closely to skin (ordinary) | 5 | 8 | 10 | 5 |
| Half of applied area was adherent closely to skin (bad) | 4 | 6 | 1 | 12 |
| More than half was separated from a skin (very bad) | 0 | 4 | 1 | 2 |
| ≧ Ordinary (%) | 16 (80) | 10 (50) | 18 (90) | 6 (30) |

Test 5

Pharmaceutical Preparation Stability

The patches of examples and comparative examples were sealed with an aluminum laminate film and preserved at 40° C. in a thermostat bath. During the period of 3 months from manufacturing, the component stability and the external character change were estimated. The component stability was confirmed with a HPLC(High pressure Liquid Cromatography) method, and the external character change was confirmed with viewing the patchs. As shown in Tables 8 and 9, it was found that the patches according to the present invention had excellent pharmaceutical preparation stability compared to that of the comparative example.

TABLE 8

Component stability (%)

| Specimen | Intial amount | 1 month | 2 months | 3 months |
|---|---|---|---|---|
| Ex. 1 | 98.5 | 96.7 | 95.9 | 94.1 (4.4) |
| Ex. 2 | 97.1 | 96.1 | 95.4 | 93.3 (3.8) |
| Ex. 3 | 98.4 | 96.5 | 95.2 | 94.9 (3.5) |
| Ex. 4 | 98.3 | 96.8 | 95.6 | 94.3 (4.0) |
| Comp. Ex. 1 | 98.4 | 96.7 | 95.8 | 94.3 (4.1) |
| Comp. Ex. 2 | 99.3 | 97.5 | 95.7 | 93.9 (5.4) |
| Comp. Ex. 3 | 99.2 | 97.3 | 95.2 | 93.0 (6.1) |

Note 1. It was estimated with the standard that ketoprofen 30 mg per solid 10 g was contained.
Note 2. The measured value is an average of three times measured.
Note 3. The number in ( ) is the value dropped compared to the intial amount.

TABLE 9

External character change

| Specimen | In manufacturing (external character) | Denaturation & spoilage | | | Deposition | | |
|---|---|---|---|---|---|---|---|
| | | 1 m. | 2 m. | 3 m. | 1 m. | 2 m. | 3 m. |
| Ex. 1 | Colorless, Almost transparentness | − | − | − | − | − | − |
| Ex. 2 | Colorless, Almost transparentness | − | − | − | − | − | − |
| Ex. 3 | Colorless, Almost transparentness | − | − | − | − | − | − |
| Ex. 4 | Colorless, Almost transparentness | − | − | − | − | − | − |
| C. Ex. 1 | White, Translucent | − | − | ± | + | ++ | +++ |
| C. Ex. 2 | White, Translucent | − | − | ± | + | ++ | +++ |
| C. Ex. 3 | White, Translucent | − | − | − | − | + | ++ |

(Criteria:
(−) No change,
(±) Little change,
(+) Considerable change)

Effect of the Invention

The invention provides a patch of a nonsteroidal antiinflammatory drug which has strong antiinflammatory action, excellent dermal absorption and skin adhesion, and has hardly any the skin irritation.

What is claimed is:

1. A transdermal patch for delivery of a nonsteroidal drug comprising a nonsteroidal anti-inflammatory drug active component 0.1–10 weight %, alkyl-pyrrolidone 0.5–10 weight %, hydrophilic polyalkylene glycol 1–15 weight %, hydrophilic nonionic surfactant 0.01–3 weight %, water soluble polymer having carboxyl group 2–15 weight %, water soluble vinyl polymer 0.1–10 weight %, water insoluble multivalent metallic salt 0.01–10 weight %, multivalent alcohol 4–40 weight % and organic hydroxy acid and water.

2. A patch as claimed in claim 1, characterized in that said active component of nonsteroidal antiinflammatory drug is selected from ketoprofen, flurbirprofen, piroxycam, tenoxicam, diclophenac and ferbinac.

3. A patch as claimed in claim 1, characterized in that said alkyl-pyrrolidone is selected from one or more of methyl-pyrrolidone, ethyl-pyrrolidone, 2-hydroxyethy-pyrrolidone.

4. A patch as claimed in claim 1, characterized in that said hydrophilic nonionic surfactant is selected from polyoxyethylene glycerin fatty acid ester, poly glycerin fatty acid ester, polyoxyethylenesorbitane fatty acid ester, polyoxyethylenesorbitol fatty acid ester, polyoxyethylene glycol fatty acid ester, polyoxyethylene castor oil/or curing castor oil, polyoxyethylenealkyl ester, polyoxyethylenealkylphenyl ether and polyoxyethylene polyoxypropylenealkyl ether, of which HLB is 10 and more.

5. A patch as claimed in claim 1, characterized in that said carboxyl group including water soluble polymer material is selected one or more from polyacrylic acid, sodium polyacrylate, partial neutralization of sodium polyacrylate and sodium carboxymethyl cellulose.

6. A patch as claimed in claim 1, characterized in that said water soluble vinyl polymer is selected from one or more of polyvinyl alcohol, polyvinyl-pyrrolidone and vinylpyrrolidone/vinylacetate copolymer.

7. A patch as claimed in claim 1, characterized in that said water insoluble multivalent metal salt is selected from one or more of aluminum hydroxide, aluminum sulfide, aluminum nitrate, aluminum acetate, sodium aluminate and aluminum glycinate, magnesium hydroxide, magnesium sulfide, magnesium nitrate, calcium hydroxide, calcium carbonate, calcium citrate, calcium cirtate and calcium panthothenate.

8. A patch as claimed in claim 1, characterized in that said organic hydroxy acid is selected from tartaric acid, citric acid, lactic acid, malic acid, gluconic acid and glycolic acid.

9. A patch as claimed in claim 1, characterized in that said multivalent alcohol is selected from ethylene glycol, propylene glycol, 1,3-butanediol, triethylene glycol, glycerin, nonlyglycerin, trihydroxyisobutane, erythritol, pentaerythritol, xylitol, adonitol, sorbitol and mannitol.

10. A transdermal patch for delivery of a nonsteroidal drug comprising a nonsteroidal anti-inflammatory drug active component 0.1–1.0 weight %, alkyl-pyrrolidone 0.5–10 weight %, hydrophilic glycol 1–15 weight %, hydrophilic nonionic surfactant 0.01–3 weight %, water soluble polymer having carboxyl group 2–15 weight %, water soluble vinyl polymer 0.1–10 weight %, water insoluble multivalent metallic salt 0.01–10 weight %, multivalent alcohol 4–40 weight % and organic hydroxy acid and water, wherein said hydrophilic glycol is selected from polyethylene glycol, polypropylene glycol and polybutylene glycol.

11. A patch as claimed in claim 10, characterized in that said active component of nonsteroidal anti-inflammatory drug is selected from ketoprofen, flurbirprofen, piroxycam, tenoxicam, diclophenac and ferbinac.

12. A patch as claimed in claim 10, characterized in that said alkyl-pyrrolidone is one or more of methyl-pyrrolidone, ethyl-pyrrolidone, and 2-hydroxyethy-pyrrolidone.

13. A patch as claimed in claim 10, characterized in that said hydrophilic nonionic surfactant is selected from polyoxyethylene glycerin fatty acid ester, poly glycerin fatty acid ester, polyoxyethylenesorbitane fatty acid ester, polyoxyethylenesorbitol fatty acid ester, polyoxyethylene glycol fatty acid ester, polyoxyethylene caster oil/or curing castor oil, polyoxyethylenealkyl ester, polyoxyethylenealkylphenyl ether and polyoxyethylene polyoxypropylenealkyl ether, of which HLB is 10 and more.

14. A patch as claimed in claim 10, characterized in that said water soluble polymer having carboxyl group is selected from one or more of polyacrylic acid, sodium polyacrylate, partial neutralization of sodium polyacrylate and sodium carboxymethyl cellulose.

15. A patch as claimed in claim 10, characterized in that said water soluble vinyl polymer is selected from one or more of polyvinyl alcohol, polyvinyl-pyrrolidone copolymer and vinylpyrrolidone-vinylacetate copolymer.

16. A patch as claimed in claim 10, characterized in that said water insoluble multivalent metal salt is selected from one or more of aluminum hydroxide, aluminum sulfide, aluminum nitrate, aluminum acetate, sodium aluminate, aluminum glycinate, magnesium hydroxide, magnesium sulfide, magnesium nitrate, calcium hydroxide, calcium carbonate, calcium nitrate, calcium citrate and calcium pantothenate.

17. A patch as claimed in claim 10, characterized in that said organic hydroxy acid is selected from tartaric acid, citric acid, lactic acid, malic acid, gluconic acid and glycolic acid.

18. A patch as claimed in claim 10, characterized in that said multivalent alcohol is selected from ethylene glycol, propylene glycol, 1,3-butanediol, triethylene glycol, glycerin, nonlyglycerin, trihydroxyisobutane, erythritol, pentaerythritol, xylitol, adonitol, sorbitol and mannitol.

* * * * *

UNITED STATES PATENT AND TRADEMARK OFFICE
CERTIFICATE OF CORRECTION

PATENT NO.   : 6,455,067 B1
DATED        : September 24, 2002
INVENTOR(S)  : Yang Pyo Woo et al.

It is certified that error appears in the above-identified patent and that said Letters Patent is hereby corrected as shown below:

Column 13,
Line 60, "component 0.1-10 weight %" should read -- component 0.1-1.0 weight % --.

Column 14,
Lines 31 and 32, "calcium citrate, calcium cirtate and" should read
-- calcium nitrate, calcium cirtate and --.

Signed and Sealed this

Third Day of June, 2003

JAMES E. ROGAN
*Director of the United States Patent and Trademark Office*